United States Patent
Yeager et al.

(10) Patent No.: US 9,442,311 B2
(45) Date of Patent: Sep. 13, 2016

(54) CONTACT LENS WITH CAPACITIVE GAZE TRACKING

(71) Applicant: VERILY LIFE SCIENCES LLC, Mountain View, CA (US)

(72) Inventors: Daniel J. Yeager, Berkeley, CA (US); Brian Otis, Saratoga, CA (US); William J. Biederman, Fox Island, WA (US); Nathan Pletcher, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 3 days.

(21) Appl. No.: 14/587,664

(22) Filed: Dec. 31, 2014

(65) Prior Publication Data
US 2015/0362750 A1    Dec. 17, 2015

Related U.S. Application Data

(60) Provisional application No. 62/012,005, filed on Jun. 13, 2014, provisional application No. 62/012,033, filed on Jun. 13, 2014.

(51) Int. Cl.
*G02C 7/04* (2006.01)
*G02C 7/08* (2006.01)
*A61B 3/113* (2006.01)

(52) U.S. Cl.
CPC .............. *G02C 7/083* (2013.01); *A61B 3/113* (2013.01); *G02C 7/04* (2013.01)

(58) Field of Classification Search
CPC ........ G02C 7/04; G02C 7/083; G02C 11/10; G02C 7/00; G02C 7/101
USPC ......... 351/159.03, 159.04, 159.02; 623/6.22, 623/6.11
See application file for complete search history.

(56) References Cited

U.S. PATENT DOCUMENTS 7,311,398 B2    12/2007 Kuiper et al.
8,634,145 B2    1/2014 Pugh et al.
(Continued)

FOREIGN PATENT DOCUMENTS

| EP | 2 518 555 A1 | 10/2012 |
| WO | WO 2007/107589 A1 | 9/2007 |
| WO | WO 2012/051167 A1 | 4/2012 |

OTHER PUBLICATIONS

De Smet, J. et al., "Progress toward a liquid crystal contact lens display", Journal of the SID 21/9, DOI: 10.1002/jsid.188, 2014 pp. 399-406.

De Smet, J. et al., "A Liquid Crystal Based Contact Lens Display Using PEDOT: PSS and Obliquely Evaporated SiO2", Late-News Poster, SID 2012 Digest, pp. 1375-1378.

(Continued)

*Primary Examiner* — Hung Dang
(74) *Attorney, Agent, or Firm* — Blakely Sokoloff Taylor & Zafman LLP

(57) ABSTRACT

An eye-mountable device includes an enclosure material, a capacitive sensor system, and a controller. The enclosure material has a concave surface and a convex surface. The concave surface is configured to be removeably mounted over a cornea and the convex surface is configured to be compatible with eyelid motion when the concave surface is so mounted. The capacitive sensor system is disposed within the enclosure material. The capacitive sensor system has at least one capacitance value that varies with changes in a gazing direction of the cornea. The controller is disposed within the enclosure material and electrically connected to the capacitive sensor system. The controller is configured to measure the capacitance value of the capacitive sensor system to detect the changes in the gazing direction.

28 Claims, 8 Drawing Sheets

(56) References Cited

U.S. PATENT DOCUMENTS

| | | |
|---|---|---|
| 8,636,358 B2 | 1/2014 | Binder |
| 8,919,953 B1 | 12/2014 | Ho |
| 2004/0027536 A1 | 2/2004 | Blum et al. |
| 2005/0099594 A1* | 5/2005 | Blum ............... B29D 11/00826 351/159.03 |
| 2012/0075712 A1 | 3/2012 | Pugh et al. |
| 2012/0140167 A1 | 6/2012 | Blum |
| 2012/0245444 A1 | 9/2012 | Otis et al. |
| 2012/0268712 A1 | 10/2012 | Egan et al. |
| 2012/0310339 A1 | 12/2012 | Berge |
| 2013/0258275 A1 | 10/2013 | Toner et al. |
| 2013/0258277 A1 | 10/2013 | Pugh et al. |
| 2014/0107447 A1 | 4/2014 | Liu et al. |
| 2014/0107448 A1 | 4/2014 | Liu et al. |
| 2014/0192311 A1 | 7/2014 | Pletcher et al. |
| 2014/0192312 A1 | 7/2014 | Pletcher et al. |
| 2014/0192318 A1 | 7/2014 | Guth et al. |
| 2014/0194773 A1 | 7/2014 | Pletcher et al. |
| 2014/0209481 A1 | 7/2014 | Pletcher et al. |
| 2014/0213867 A1 | 7/2014 | Pletcher et al. |
| 2014/0240655 A1 | 8/2014 | Pugh et al. |
| 2014/0240665 A1 | 8/2014 | Pugh et al. |
| 2014/0243971 A1 | 8/2014 | Pugh et al. |
| 2014/0327875 A1 | 11/2014 | Blum et al. |

OTHER PUBLICATIONS

Milton, H. et al., "Optimization of refractive liquid crystal lenses using an efficient multigrid simulation", May 2012, vol. 20, No. 10, Optics Express, pp. 11159-11165.

Milton, H. et al., "Switchable liquid crystal contact lenses: dynamic vision for the ageing eye", Proc. of SPIE vol. 9004 90040H, 6 pages. Downloaded From: http://spiedigitallibrary.org/ on Mar. 28, 2014.

Milton, H. et al., "Electronic liquid crystal contact lenses for the correction of presbyopia", Apr. 2014, vol. 22, No. 7, DOI:10.1364/OE.22.008035, Optics Express, pp. 8035-8040.

Tremblay, E. et al. "Switchable telescopic contact lens", Jul. 2013, vol. 21, No. 13, DOI:10.1364/OE.21.015980, Optics Express, pp. 15980-15986.

PCT/US2015/031231—International Search Report and Written Opinion, mailed Aug. 26, 2015, 19 pages.

PCT/US2015/031232—International Search Report and Written Opinion, mailed Aug. 26, 2015, 22 pages.

U.S. Appl. No. 14/587,639—Non-Final Office Action, mailed Jan. 20, 2016, 12 pages.

Biederman, William J. et al., Capacitive Gaze Tracking for Auto-Accommodation in a Contact Lens, U.S. Appl. No. 14/587,639, filed Dec. 31, 2014, whole document.

\* cited by examiner

CONTACT LENS WITH CAPACITIVE GAZE TRACKING

CROSS-REFERENCE TO RELATED APPLICATIONS

This application claims priority under the provisions of 35 U.S.C. §119(e) to U.S. Provisional Application No. 62/012,005, filed on Jun. 13, 2014, entitled "Accommodating Lens," and to U.S. Provisional Application No. 62/012,033, filed on Jun. 13, 2014, entitled "Accommodating Lens Fabrication."

TECHNICAL FIELD

This disclosure relates generally to the field of optics, and in particular but not exclusively, relates to contact lenses.

BACKGROUND INFORMATION

Accommodation is a process by which the eye adjusts its focal distance to maintain focus on objects of varying distance. Accommodation is a reflex action, but can be consciously manipulated. Accommodation is controlled by contractions of the ciliary muscle. The ciliary muscle encircles the eye's elastic lens and applies a force on the elastic lens during muscle contractions that change the focal point of the elastic lens.

As an individual ages, the effectiveness of the ciliary muscle degrades. Presbyopia is a progressive age-related loss of accommodative or focusing strength of the eye, which results in increased blur at near distances. This loss of accommodative strength with age has been well studied and is relatively consistent and predictable. Presbyopia affects nearly 1.7 billion people worldwide today (110 million in the United States alone) and that number is expected to substantially rise as the world's population ages. Techniques and devices that can help individuals offset the effects of Presbyopia are increasingly in demand.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

DETAILED DESCRIPTION

Figure 1:
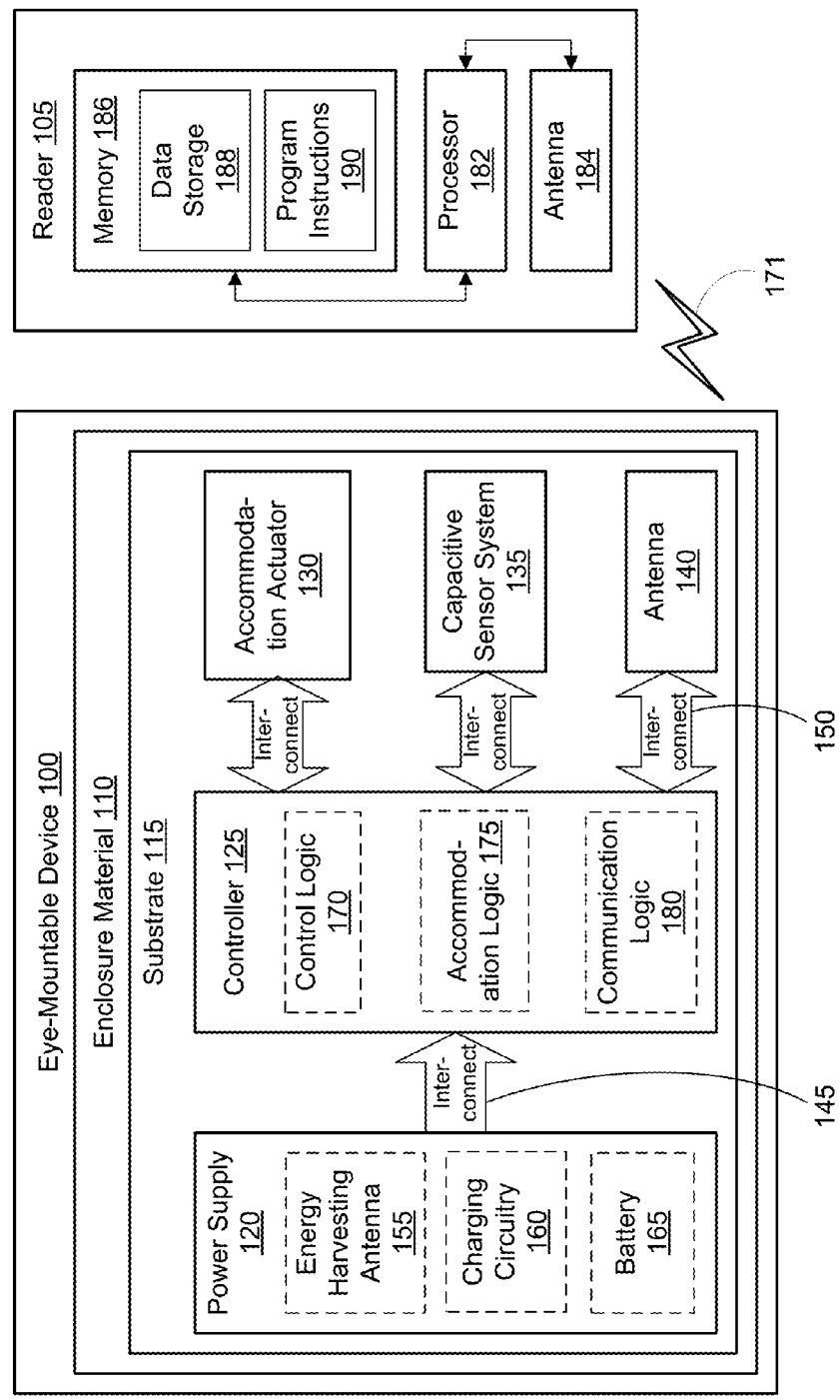
FIG. 1 is a functional block diagram of an eye-mountable device with capacitive gaze tracking for auto-accommodation along with an external reader, in accordance with an embodiment of the disclosure.

Embodiments of an apparatus, system and methods of operation for a contact lens with capacitive gaze tracking and accommodation are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Described herein is a smart contact lens or eye-mountable device that includes gaze detection circuitry and logic for identifying the direction or focal distance of a user's gaze and using this information for real-time feedback control of an accommodation actuator. Embodiments of the eye-mountable device may include power supply circuitry, control electronics, an accommodation actuator, a capacitive sensor system, and an antenna all embedded within an enclosure material formed to be contact mounted to an eye. The control electronics are coupled to monitor the capacitive sensor system to identify gaze direction/focal distance, manipulate the accommodation actuator to control the optical power of the eye-mountable device, and provide wireless communications with an external reader. In some embodiments, the power supply may include charging circuitry for controlling inductive wireless charging of an embedded battery.

The enclosure material may be fabricated of a variety of materials compatible for direct contact with a human eye, such as a polymeric material, a hydrogel, PMMA, silicone based polymers (e.g., fluoro-silicon acrylate), or otherwise. The enclosure material can be in the form of a round lens with a concave curvature configured to mount to a corneal surface of an eye. The electronics can be disposed upon a substrate embedded within the enclosure material near its periphery to avoid interference with incident light received closer to the central region of the cornea. The capacitive sensor system can be arranged on the substrate to face outward towards the eyelids to detect the gaze direction/focal distance based upon the amount and position of eyelid coverage over the capacitive sensor system. As the eyelids cover different portions of the capacitive sensor system, this changes its capacitance, which can be measured to determine gaze direction and/or focal distance.

In some embodiments, the gaze direction/focal distance information can then be used to determine the amount of accommodation to be applied via a see-through accommodation actuator positioned in a central portion of the enclosure material. The accommodation actuator is coupled to the controller to be electrically manipulated thereby. For example, the accommodation actuator maybe implemented with a liquid crystal cell that changes its index of refraction in response to an applied electrical bias signal. In other embodiments, the accommodation actuator may be implemented using other types of electro-active optical materials such as electro-optic materials that vary refractive index in the presence of an applied electric field or electro-mechanical structures that change the shape of a deformable lens. Other example structures that may be used to implement the accommodation actuator include electro-wetting optics, micro-electro-mechanical systems, or otherwise.

FIG. 1 is a functional block diagram of an eye-mountable device 100 with capacitive gaze tracking for auto-accommodation along with an external reader 105, in accordance with an embodiment of the disclosure. The exposed portion of eye-mountable device 100 is an enclosure material 110 formed to be contact-mounted to a corneal surface of an eye. A substrate 115 is embedded within or surrounded by enclosure material 110 to provide a mounting surface for a power supply 120, a controller 125, an accommodation actuator 130, a capacitive sensor system 135, an antenna 140, and various interconnects 145 and 150. The illustrated embodiment of power supply 120 includes an energy harvesting antenna 155, charging circuitry 160, and a battery 165. The illustrated embodiment of controller 125 includes control logic 170, accommodation logic 175, and communication logic 180. The illustrated embodiment of reader 105 includes a processor 182, an antenna 184, and memory 186. The illustrated embodiment of memory 186 includes data storage 188 and program instructions 190.

Controller 125 is coupled to receive feedback control signals from capacitive sensor system 135 and further coupled to operate accommodation actuator 130. Power supply 120 supplies operating voltages to the controller 125 and/or the accommodation actuator 130. Antenna 140 is operated by the controller 125 to communicate information to and/or from eye-mountable device 100. In one embodiment, antenna 140, controller 125, power supply 120, and capacitive sensor system 135 are all situated on the embedded substrate 115. In one embodiment, accommodation actuator 130 is embedded within enclosure material 110, but is not disposed on substrate 115. Because eye-mountable device 100 includes electronics and is configured to be contact-mounted to an eye, it is also referred to herein as an ophthalmic electronics platform, contact lens, or smart contact lens.

To facilitate contact-mounting, the enclosure material 110 can have a concave surface configured to adhere ("mount") to a moistened corneal surface (e.g., by capillary forces with a tear film coating the corneal surface). Additionally or alternatively, the eye-mountable device 100 can be adhered by a vacuum force between the corneal surface and enclosure material 110 due to the concave curvature. While mounted with the concave surface against the eye, the outward-facing surface of the enclosure material 110 can have a convex curvature that is formed to not interfere with eye-lid motion while the eye-mountable device 100 is mounted to the eye. For example, the enclosure material 110 can be a substantially transparent curved disk shaped similarly to a contact lens.

Enclosure material 110 can include one or more biocompatible materials, such as those employed for use in contact lenses or other ophthalmic applications involving direct contact with the corneal surface. Enclosure material 110 can optionally be formed in part from such biocompatible materials or can include an outer coating with such biocompatible materials. Enclosure material 110 can include materials configured to moisturize the corneal surface, such as hydrogels and the like. In some instances, enclosure material 110 can be a deformable ("non-rigid") material to enhance wearer comfort. In some instances, enclosure material 110 can be shaped to provide a predetermined, vision-correcting optical power, such as can be provided by a contact lens. Enclosure material may be fabricated of various materials including a polymeric material, a hydrogel, PMMA, silicone based polymers (e.g., fluoro-silicon acrylate), or otherwise.

Substrate 115 includes one or more surfaces suitable for mounting the capacitive sensor system 135, controller 125, power supply 120, and antenna 140. Substrate 115 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide) can be patterned on substrate 115 to form circuitry, electrodes, etc. For example, antenna 140 can be formed by depositing a pattern of gold or another conductive material on substrate 115. Similarly, interconnects 145 and 150 can be formed by depositing suitable patterns of conductive materials on substrate 115. A combination of resists, masks, and deposition techniques can be employed to pattern materials on substrate 115. Substrate 115 can be a relatively rigid material, such as polyethylene terephthalate ("PET") or another material sufficient to structurally support the circuitry and/or electronics within enclosure material 110. Eye-mountable device 100 can alternatively be arranged with a group of unconnected substrates rather than a single substrate. For example, controller 125 and power supply 120 can be mounted to one substrate, while antenna 140 and capacitive sensor system 135 are mounted to another substrate and the two can be electrically connected via interconnects.

In some embodiments, power supply 120 and controller 125 (and the substrate 115) can be positioned away from the center of eye-mountable device 100 and thereby avoid interference with light transmission to the eye through the center of eye-mountable device 110. In contrast, accommodation actuator 130 can be centrally positioned to apply optical accommodation to the light transmitted to the eye through the center of eye-mountable device 110. For example, where eye-mountable device 100 is shaped as a concave-curved disk, substrate 115 can be embedded around the periphery (e.g., near the outer circumference) of the disk. In some embodiments, capacitive sensor system 135 includes one or more discrete capacitance sensors that are peripherally distributed to sense the eyelid overlap. In some embodiments, one or more capacitance sensors may also be positioned in the center region of eye-mountable device 100.

Capacitive sensor system 135 and/or substrate 115 can be substantially transparent to incoming visible light to mitigate interference with light transmission to the eye.

Substrate 115 can be shaped as a flattened ring with a radial width dimension sufficient to provide a mounting platform for the embedded electronics components. Substrate 115 can have a thickness sufficiently small to allow the substrate to be embedded in enclosure material 110 without adversely influencing the profile of eye-mountable device 100. Substrate 115 can have a thickness sufficiently large to provide structural stability suitable for supporting the electronics mounted thereon. For example, substrate 115 can be shaped as a ring with a diameter of about 10 millimeters, a radial width of about 1 millimeter (e.g., an outer radius 1 millimeter larger than an inner radius), and a thickness of about 50 micrometers. Substrate 115 can optionally be aligned with the curvature of the eye-mounting surface of eye-mountable device 100 (e.g., convex surface). For example, substrate 115 can be shaped along the surface of an imaginary cone between two circular segments that define an inner radius and an outer radius. In such an example, the surface of substrate 115 along the surface of the imaginary cone defines an inclined surface that is approximately aligned with the curvature of the eye mounting surface at that radius.

In the illustrated embodiment, power supply 120 includes a battery 165 to power the various embedded electronics, including controller 125. Battery 165 may be inductively charged by charging circuitry 160 and energy harvesting antenna 155. In one embodiment, antenna 140 and energy harvesting antenna 155 are independent antennae, which serve their respective functions of energy harvesting and communications. In another embodiment, energy harvesting antenna 155 and antenna 140 are the same physical antenna that are time shared for their respective functions of inductive charging and wireless communications with reader 105. Additionally or alternatively, power supply 120 may include a solar cell ("photovoltaic cell") to capture energy from incoming ultraviolet, visible, and/or infrared radiation. Furthermore, an inertial power scavenging system can be included to capture energy from ambient vibrations.

Charging circuitry 160 may include a rectifier/regulator to condition the captured energy for charging battery 165 or directly power controller 125 without battery 165. Charging circuitry 160 may also include one or more energy storage devices to mitigate high frequency variations in energy harvesting antenna 155. For example, one or more energy storage devices (e.g., a capacitor, an inductor, etc.) can be connected to function as a low-pass filter.

Controller 125 contains logic to choreograph the operation of the other embedded components. Control logic 170 controls the general operation of eye-mountable device 100, including providing a logical user interface, power control functionality, etc. Accommodation logic 175 includes logic for monitoring feedback signals from capacitive sensor system 135, determining the current gaze direction or focal distance of the user, and manipulating accommodation actuator 130 in response to provide the appropriate accommodation. The auto-accommodation can be implemented in real-time based upon feedback from the capacitive gaze tracking, or permit user control to select specific accommodation regimes (e.g., near-field accommodation for reading, far-field accommodation for regular activities, etc.). Communication logic 180 provides communication protocols for wireless communication with reader 105 via antenna 140. In one embodiment, communication logic 180 provides backscatter communication via antenna 140 when in the presence of an electromagnetic field 171 output from reader 105. In one embodiment, communication logic 180 operates as a smart wireless radio-frequency identification ("RFID") tag that modulates the impedance of antenna 140 for backscatter wireless communications. The various logic modules of controller 125 may be implemented in software/firmware executed on a general purpose microprocessor, in hardware (e.g., application specific integrated circuit), or a combination of both.

Eye-mountable device 100 may include various other embedded electronics and logic modules. For example, a light source or pixel array may be included to provide visible feedback to the user. An accelerometer or gyroscope may be included to provide positional, rotational, directional or acceleration feedback information to controller 125.

It is noted that the block diagram shown in FIG. 1 is described in connection with functional modules for convenience in description, but does not necessarily connote physical organization. Rather, embodiments of eye-mountable device 100 can be arranged with one or more of the functional modules ("sub-systems") implemented in a single chip, multiple chips, in one or more integrated circuits, or otherwise.

External reader 105 includes an antenna 184 (or group of more than one antennae) to send and receive wireless signals 171 to and from eye-mountable device 100. External reader 105 also includes a computing system with a processor 182 in communication with a memory 186. Memory 186 is a non-transitory computer-readable medium that can include, without limitation, magnetic disks, optical disks, organic memory, and/or any other volatile (e.g. RAM) or non-volatile (e.g. ROM) storage system readable by the processor 182. Memory 186 can include a data storage 188 to store indications of data, such as data logs (e.g., user logs), program settings (e.g., to adjust behavior of eye-mountable device 100 and/or external reader 105), etc. Memory 186 can also include program instructions 190 for execution by processor 182 to cause the external reader 105 to perform processes specified by the instructions 190. For example, program instructions 190 can cause external reader 105 to provide a user interface that allows for retrieving information communicated from eye-mountable device 100 or allows transmitting information to eye-mountable device 100 to program or otherwise select operational modes of eye-mountable device 100. External reader 105 can also include one or more hardware components for operating antenna 184 to send and receive wireless signals 171 to and from eye-mountable device 100.

External reader 105 can be a smart phone, digital assistant, or other portable computing device with wireless connectivity sufficient to provide the wireless communication link 171. External reader 105 can also be implemented as an antenna module that can be plugged in to a portable computing device, such as in an example where the communication link 171 operates at carrier frequencies not commonly employed in portable computing devices. In some instances, external reader 105 is a special-purpose device configured to be worn relatively near a wearer's eye to allow the wireless communication link 171 to operate with a low power budget. For example, the external reader 105 can be integrated in a piece of jewelry such as a necklace, earing, etc. or integrated in an article of clothing worn near the head, such as a hat, headband, etc.

Figure 2A:
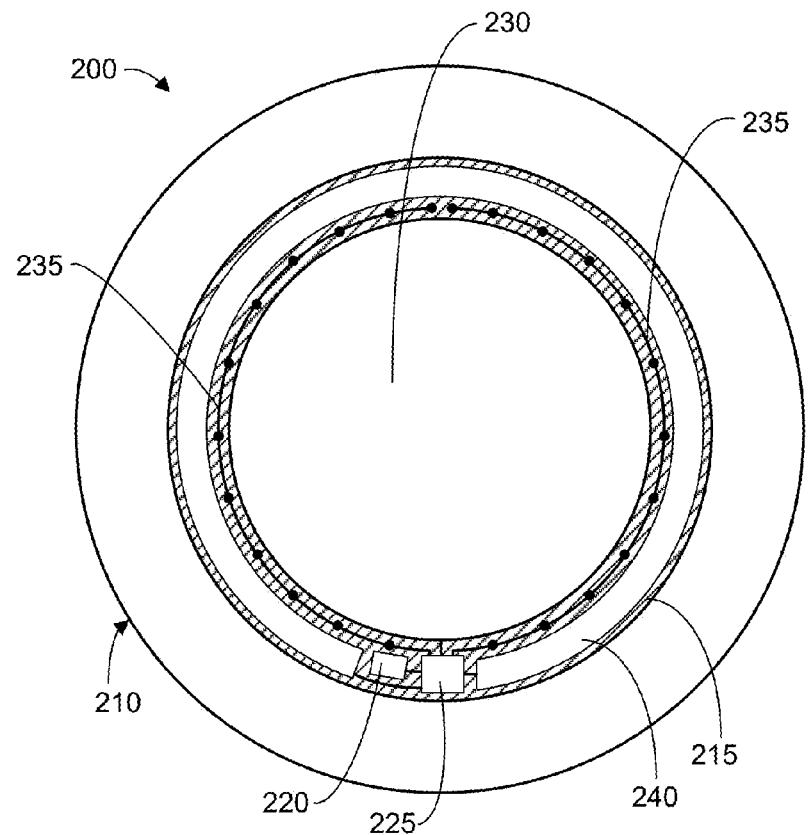
FIG. 2A is a top view of an eye-mountable device, in accordance with an embodiment of the disclosure.
Figure 2B:
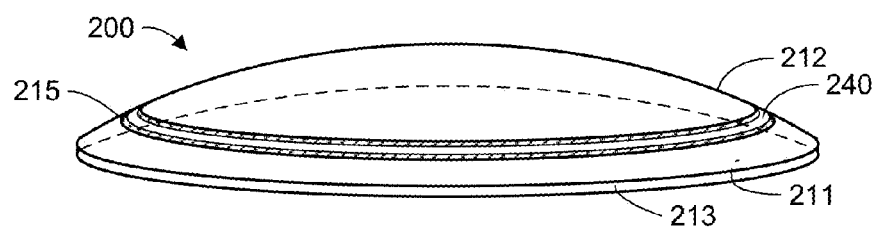
FIG. 2B is a perspective view of an eye-mountable device, in accordance with an embodiment of the disclosure.

FIGS. 2A and 2B illustrate two views of an eye-mountable device 200, in accordance with an embodiment of the disclosure. FIG. 2A is a top view of eye-mountable device 200 while FIG. 2B is a perspective view of the same.

Eye-mountable device 200 is one possible implementation of eye-mountable device 100 illustrated in FIG. 1. The illustrated embodiment of eye-mountable device 200 includes an enclosure material 210, a substrate 215, a power supply 220, a controller 225, an accommodation actuator 230, a capacitive sensor system 235, and an antenna 240. It should be appreciated that FIGS. 2A and 2B are not necessarily drawn to scale, but have been illustrated for purposes of explanation only in describing the arrangement of the example eye-mountable device 200.

Enclosure material 210 of eye-mountable device 200 is shaped as a curved disk. Enclosure material 210 is a substantially transparent material to allow incident light to be transmitted to the eye while eye-mountable device 200 is mounted to the eye. Enclosure material 210 is a biocompatible material similar to those employed to form vision correction and/or cosmetic contact lenses in optometry, such as a polymeric material, polyethylene terephthalate ("PET"), polymethyl methacrylate ("PMMA"), polyhydroxyethylmethacrylate ("polyHEMA"), a hydrogel, silicon based polymers (e.g., fluoro-silicon acrylate) combinations of these, or otherwise. Enclosure material 210 can be formed with one side having a concave surface 211 suitable to fit over a corneal surface of an eye. The opposite side of the disk can have a convex surface 212 that does not interfere with eyelid motion while eye-mountable device 200 is mounted to the eye. In the illustrated embodiment, a circular or oval outer side edge 213 connects the concave surface 211 and convex surface 212.

Eye-mountable device 200 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of eye-mountable device 200 can be selected according to the size and/or shape of the corneal surface of the wearer's eye. Enclosure material 210 can be formed with a curved shape in a variety of ways. For example, techniques similar to those employed to form vision-correction contact lenses, such as heat molding, injection molding, spin casting, etc. can be employed to form enclosure material 210.

Substrate 215 is embedded within enclosure material 210. Substrate 215 can be embedded to be situated along the outer periphery of enclosure material 210, away from the central region where accommodation actuator 230 is positioned. In the illustrated embodiment, substrate 215 encircles accommodation actuator 230. Substrate 215 does not interfere with vision because it is too close to the eye to be in focus and is positioned away from the central region where incident light is transmitted to the light-sensing portions of the eye. In some embodiments, substrate 215 can optionally be formed of a transparent material to further mitigate effects on visual perception. Substrate 215 can be shaped as a flat, circular ring (e.g., a disk with a centered hole). The flat surface of substrate 215 (e.g., along the radial width) is a platform for mounting electronics and for patterning conductive materials to form electrodes, antenna(e), and/or interconnections.

Figure 3A:
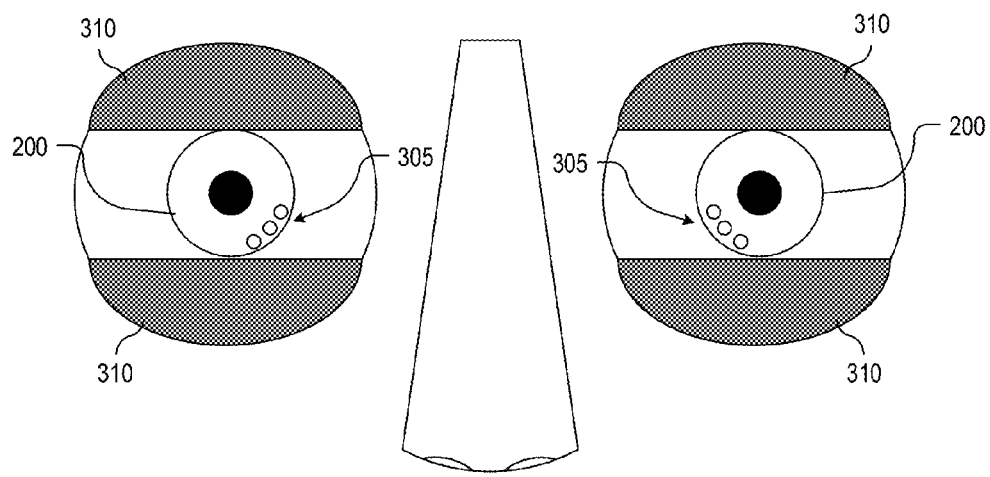
FIGS. 3A and 3B illustrate the general operation of a capacitive gaze detection mechanism, in accordance with an embodiment of the disclosure.
Figure 3B:
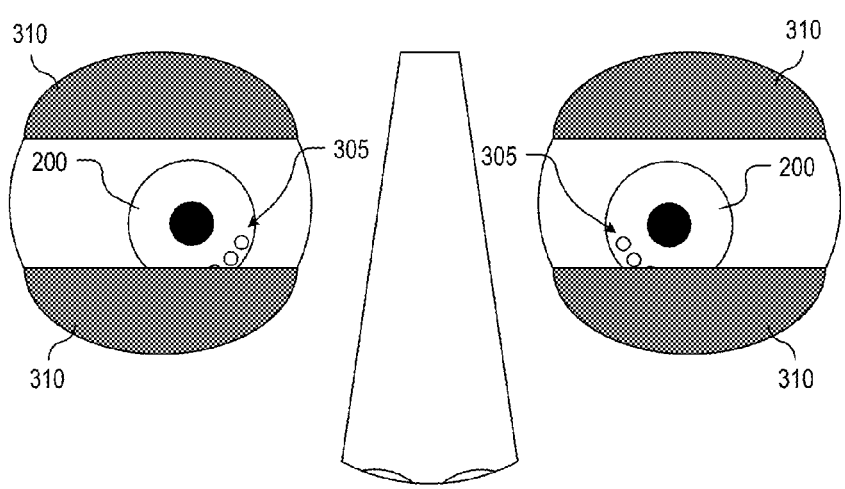

Capacitive sensor system 235 is distributed about eye-mountable device 200 to sense eyelid overlap in a manner similar to capacitive touch screens. By monitoring the amount and position of eyelid overlap, feedback signals from capacitive sensor system 235 can be measured by controller 225 to determine the approximate gaze direction and/or focal distance. Referring to FIG. 3A, eye-mountable device 200 is disposed on a cornea that is looking straight forward. In this position, capacitance sensors 305 are not overlapped by eyelids 310, which influences their capacitance value. Controller 225 can determine that the cornea is looking straight forward via the feedback signals from capacitance sensors 305. In this scenario, controller 224 may determine that the user is focusing on the far-field and the accommodation adjusted accordingly. Correspondingly (see FIG. 3B), if controller 225 determines, based upon the amount and locations of eyelid 310 overlap of capacitance sensors 305, that the cornea is looking down and inward towards the nose, then it can be assumed the user is focusing on the near-field (e.g., reading). In this scenario, the amount of accommodation applied by accommodation actuator 230 should correspond to a near-field focal distance associated with the activity of reading.

Capacitive sensor system 235 is disposed within enclosure material 210 on substrate 215. In the illustrated embodiment, capacitive sensor system 235 is distributed peripherally around accommodation actuator 230. In the illustrated embodiment, capacitive sensor system 235 is disposed along the inner edge of substrate 215 between antenna 240 and accommodation actuator 230. In other embodiments, capacitive sensor system 235 may be partially or entirely distributed along the outer edge of substrate 215 peripherally to antenna 240. Capacitive sensor system 235 may be disposed on the backside of substrate 215 adjacent to concave surface 211 or on the frontside of substrate 215 adjacent to convex surface 212. Several orientations, groupings, and distributions may be used to implement capacitive sensor system 235. In the illustrated embodiment, capacitive sensor system 235 includes a plurality of discrete capacitance sensors coupled to a common read-line; however, various implementations include a single elongated capacitance sensor, a plurality of discrete capacitance sensors, multiple discrete capacitance sensors coupled in parallel via a common read-line, multiple independent branches of parallel coupled discrete capacitance sensors, etc. These and other implementations for capacitive sensor system 235 are discussed in further detail below in connection with FIGS. 6A-6E.

Accommodation actuator 230 is centrally positioned within enclosure material 210 to affect the optical power of eye-mountable device 200 in the user's center of vision. In various embodiments, accommodation actuator 230 operates by changing is index of refraction under the influence of controller 225. By changing its refractive index, the net optical power of the curved surfaces of eye-mountable device 200 is altered, thereby applying controllable accommodation. Accommodation actuator 230 may be implemented using a variety of different electro-active optical devices. For example, accommodation actuator 230 may be implemented using a layer of liquid crystal (e.g., a liquid crystal cell) disposed in the center of enclosure material 210. In other embodiments, accommodation actuator 230 may be implemented using other types of electro-active optical materials such as electro-optic materials that vary refractive index in the presence of an applied electric field. Accommodation actuator 230 may be a distinct device embedded within enclosure material 210 (e.g., liquid crystal cell), or a bulk material having a controllable refractive index. In yet another embodiment, accommodation actuator 230 may be implemented using a deformable lens structure that changes shape under the influence of an electrical signal. Accordingly, the optical power of eye-mountable device 200 is controlled by controller 225 with the application of electric signals via one or more electrodes extending from controller 225 to accommodation actuator 230.

Accommodation actuator 230 may be implemented using a variety of different liquid crystal structures including nematic liquid crystal, nematic twisted liquid crystal, cholesteric liquid crystal, or blue phase liquid crystal. Since a low switching voltage is desirable for low power chip design, nematic liquid crystals with switching voltages less than 5 V are suitable. With the application of a 5V control signal, refractive index switching ranging from approximately 1.74 in an off-mode to 1.52 in an on-mode is achievable. A refractive index shift of 0.2 should be sufficient to provide near-field accommodation for reading.

Returning to FIG. 2A, loop antenna 240 is a layer of conductive material patterned along the flat surface of the substrate to form a flat conductive ring. In some examples, to allow additional flexibility along the curvature of the enclosure material, loop antenna 240 can include multiple substantially concentric sections electrically joined together. Each section can then flex independently along the concave/convex curvature of eye-mountable device 200. In some examples, loop antenna 240 can be formed without making a complete loop. For instances, antenna 240 can have a cutout to allow room for controller 225 and power supply 220, as illustrated in FIG. 2A. However, loop antenna 240 can also be arranged as a continuous strip of conductive material that wraps entirely around the flat surface of substrate 215 one or more times. For example, a strip of conductive material with multiple windings can be patterned on the backside of substrate 215 opposite controller 225, power supply 220, and capacitive sensor system 235. Interconnects between the ends of such a wound antenna (e.g., the antenna leads) can then be passed through substrate 215 to controller 225.

Since eye-mountable device 100 may be used by different user's having a variety of different eye sizes and eyelid shapes, a configuration process may be useful to train the system for a particular user. Accordingly, a gaze detection calibration may be executed upon an initial use (or even on a periodic basis) to acquire baseline readings for different gaze directions and focal distances.

Figure 4:
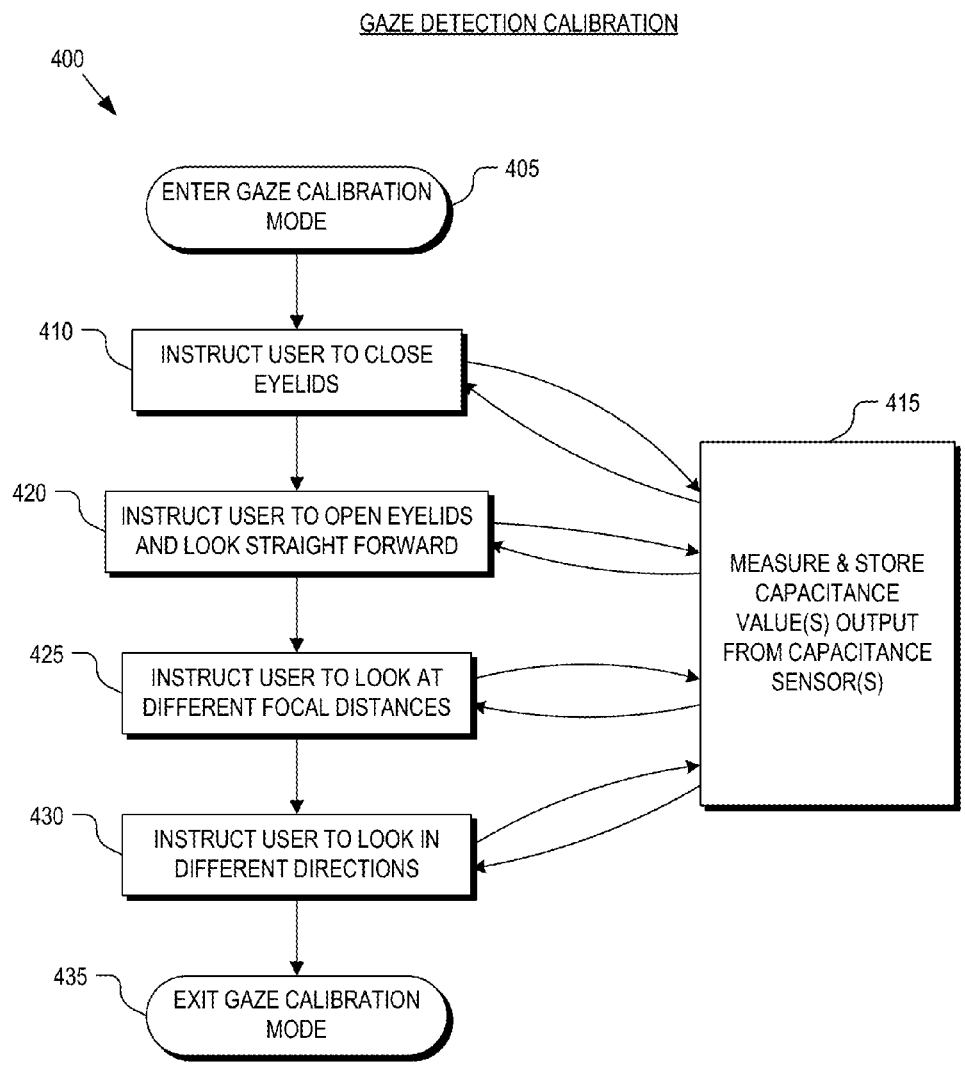
FIG. 4 is a flow chart illustrating a process for calibration of a capacitive gaze detection mechanism of an eye-mountable device, in accordance with an embodiment of the disclosure.

FIG. 4 is a flow chart illustrating a process 400 for calibration of a capacitive gaze detection mechanism of eye-mountable device 100, in accordance with an embodiment of the disclosure. The order in which some or all of the process blocks appear in process 400 should not be deemed limiting. Rather, one of ordinary skill in the art having the benefit of the present disclosure will understand that some of the process blocks may be executed in a variety of orders not illustrated, or even in parallel.

In a process block 405, controller 125 enters a gaze calibration mode. In one embodiment, gaze calibration mode is activated wirelessly via reader 105. In other embodiments, gaze calibration mode may be activated via a particular sequence of eye blinks sensed using capacitive sensor system 135. In yet other embodiments, an optical sensor may be included on substrate 115 to pick up user commands via blink sequences.

Once gaze calibration mode is engaged, the user may be prompted to position their eyes in a series of gaze directions/focal distances while baseline capacitive measurements are acquired. These capacitive measurements may be used to both associate baseline capacitance values with particular gaze directions and/or focal distances, but also to determine and/or confirm the rotational position of eye-mountable device 100. For rotational-stable contact lenses (e.g., weighted lenses or toric lenses), positional measurements may not be necessary. For non-rotationally stable contact lenses, a position calibration may be periodically re-executed or continuously monitored.

Process blocks 410 through 430 describe an example calibration sequence; however, it should be appreciated that in various other embodiments the user may be prompted to look in fewer gaze directions/focal distances, more gaze directions/focal distances, and/or alternative gaze directions/focal distances. In a process block 410, the user is prompted to close their eyelids. In one embodiment, the user may be prompted on a display screen or from an audible speaker of reader 105. In other embodiments, eye-mountable device 100 may include a pixel array capable of providing visual prompts. Once the user closes their eyelids, controller 125 measures the capacitance value(s) of capacitive sensor system 135 and stores the capacitance values as baseline reference values associated with closed eyelids (process block 415).

In a process block 420, the user is prompted to open their eyelids and look straight forward at an object that is greater than several meters away (i.e., far field object). Again, in process block 415, controller 125 measures the capacitance value(s) of capacitive sensor system 135 and stores the capacitance values as baseline reference values associated with a far-field gaze direction.

In a process block 425, the user is prompted to look at one or more different focal distance by staring at objects at a specified distance from the user. Between each prompting, process 400 returns to process block 415, where controller 125 measures the capacitance value(s) of capacitive sensor system 135 and stores the capacitance value(s) as baseline reference value(s) associated with the prompted focal distance. For example, the user may be asked to read a book and the measured capacitance value(s) are then associated with the near-field activity of reading.

In a process block 430, the user is prompted to look in one or more different directions such as up, down, left, or right. Between each prompting, process 400 returns to process block 415, where controller 125 measures the capacitance value(s) of capacitive sensor system 135 and stores the capacitance values as baseline reference value(s) associated with the prompted gaze direction. One or more of the measurements associated with process block 430 may also be executed independent of the other process blocks of process 400 to periodically determine the rotational position of eye-mountable device 100 on the cornea.

After all calibration measurements have been acquired, controller 125 exits the gaze calibration mode (process block 435).

Figure 5:
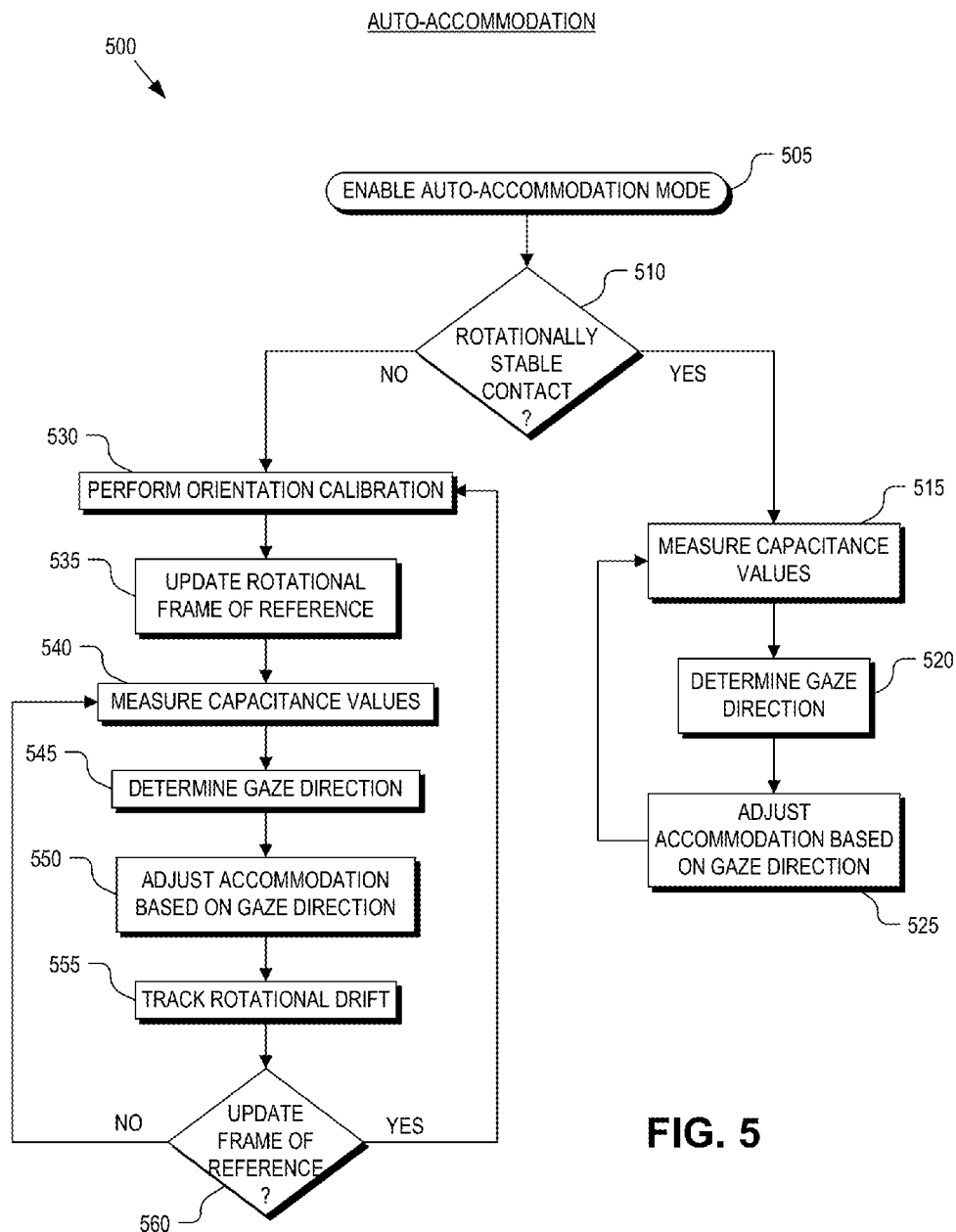
FIG. 5 is a flow chart illustrating a process of auto-accommodation based upon capacitive gaze detection feedback, in accordance with an embodiment of the disclosure.

FIG. 5 is a flow chart illustrating a process 500 for auto-accommodation using eye-mountable device 100 based upon real-time capacitive gaze detection feedback, in accordance with an embodiment of the disclosure. The order in which some or all of the process blocks appear in process 500 should not be deemed limiting. Rather, one of ordinary skill in the art having the benefit of the present disclosure will understand that some of the process blocks may be executed in a variety of orders not illustrated, or even in parallel.

In a process block 505, controller 125 enters an auto-accommodation mode. In one embodiment, the auto-accommodation mode is entered into automatically after completing a gaze detection calibration. In another embodiment, auto-accommodation mode is entered in response to a user command receive wirelessly from reader 105 or via a specific blink sequence detected via capacitive sensor system 135 or a photo-detector disposed on substrate 115 or integrated with controller 125 (not illustrated).

If eye-mountable device 100 is rotationally-stable, such as a weighted or toric contact lens (decision block 510), then process 500 continues to a process block 515. In process block 515, the capacitance value(s) of capacitive sensor system 135 are measured. In one embodiment, the capacitance values of capacitive sensor system 135 are constantly monitored and capacitive changes detected in real-time.

In a process block 520, the measured capacitance value(s) are analyzed by accommodation logic 175 with reference to the baseline values acquired during the gaze calibration mode. By comparing the measured values to the baseline calibration values, accommodation logic 175 determines the current gaze direction/focal distance of the user's eye. In a process block 525, the amount of accommodation provided by accommodation actuator 130 is adjusted based upon the determined gaze direction or focal distance. In one embodiment, the accommodation adjustments are automatic and executed in real-time under the influence of controller 125 and accommodation logic 175. As discussed above, accommodation adjustments are achieved by changing the optical power of the central portion of eye-mountable device 100. In one embodiment, the variable optical power is achieved by manipulating a refractive index of accommodation actuator 130. In other embodiments, the variable optical power may be achieved by manipulating the shape of a lens. Lens shape manipulation may be achieved via electrostatically applied force (e.g., liquid lens) or a mechanically applied force (e.g., micro-electro-mechanical-system). Other accommodation actuation mechanisms may be implemented.

Returning to decision block 510, if eye-mountable device 100 is not a rotationally-stable contact lens, then process 500 continues to a process block 530. In process block 530, controller 125 executes an orientation calibration to determine the rotational position (e.g., which direction is up relative to the eye socket or orbit) of eye-mountable device 100 on the cornea. In one embodiment, the orientation calibration may include executing the steps described in connection with process block 430 in process 400 (see FIG. 4). For example, the user may be prompted to look up or down and left or right. In other embodiments, eye-mountable device 100 may include one or more accelerometers or gyroscopes to determine its rotational direction. Once the orientation calibration has been executed, the rotational frame of references of eye-mountable device 100 is updated and temporarily stored for current operation (process block 535).

In a process block 540, the capacitance value(s) of capacitive sensor system 135 are measured. In one embodiment, the capacitance values of capacitive sensor system 135 are constantly monitored and capacitive changes detected in real-time. In a process block 545, the measured capacitance value(s) are analyzed by accommodation logic 175 with reference to the baseline values acquired during the gaze calibration mode and applying adjustments based upon the rotational frame of reference. By comparing the measured values to the baseline calibration values, accommodation logic 175 determines the current gaze direction/focal distance of the user's eye. In a process block 550, the amount of accommodation provided by accommodation actuator 130 is adjusted based upon the determined gaze direction or focal distance.

In a process block 555, controller 125 monitors or tracks rotational drift of eye-mountable device 100 on the cornea to determine if the frame of reference needs to be updated (decision block 560). Depending upon eye activity, the rate of rotational drift may vary. In one embodiment, this drift is monitored by monitoring capacitance changes in capacitive sensor system 135. When controller 125 senses the average or baseline capacitance values of capacitive sensor system 135 have changed by a threshold amount, then it may be determined that eye-mountable device 100 has sufficiently rotated to re-execute the orientation calibration in process block 530. If the average or baseline capacitance values have not deviated by the threshold amount, then process 500 returns to process block 540 to continue monitoring capacitive sensor system 135 for changes. In other embodiments, rotational drift may be tracked using embedded accelerometers, gyroscopes, or other mechanisms.

FIGS. 6A-E illustrate different capacitance sensor layouts for implementing a capacitive sensor system of an eye-mountable device, in accordance with various embodiments of the disclosure. These capacitive sensor systems represent possible implementations of capacitive sensor systems 135 or 235 illustrated in FIGS. 1 and 2A.

Figure 6A:
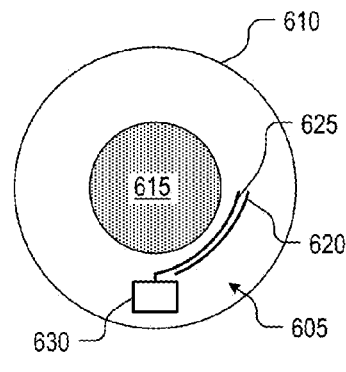
FIGS. 6A-E illustrate different capacitance sensor layouts on an eye-mountable device for a capacitive sensor system, in accordance with embodiments of the disclosure.

FIG. 6A illustrates a capacitive sensor system 605 disposed within an eye-mountable device 610. Capacitive sensor system 605 is a single elongated capacitor that partially encircles accommodation actuator 615. Capacitive sensor system 605 includes a ground electrode 620 and a read-line 625 that is coupled to a controller 630. When the cornea moves, eyelids overlap the elongated capacitor causing its capacitance value to change as a continuously changing analog value. Different capacitance values can be associated with different gazing directions or focal distances and thereby used to determine a user's gazing direction or focal distance.

In some embodiments, the separation distance between read-line 625 and ground electrode 620 is constant. In other embodiments, the separation distance between read-line 625 and ground electrode 620 varies with position. By using a variable separation distance, the linear capacitance of the capacitor changes along its length. This changing linear capacitance results in different capacitance changes when overlapped by an eyelid at different locations along its length. This variable linear capacitance provides improved differentiation for determining both position and amount of eyelid overlap and therefore improved capacitive gaze tracking.

Figure 6B:
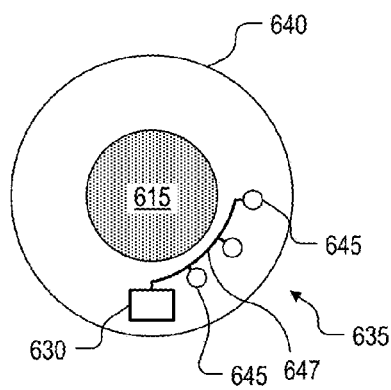

FIG. 6B illustrates a capacitive sensor system 635 disposed within an eye-mountable device 640. Capacitive sensor system 635 includes a plurality of discrete capacitance sensors 645 coupled in parallel between a common ground (not illustrated) and a common read-line 647. Each discrete capacitance sensor 645 may have the same capacitance value or a different capacitance value. When the cornea moves, eyelids overlap the various discrete capacitance sensors 645 causing the total capacitance value on read-line 647 to change. Different capacitance values can be associated with different gazing directions or focal distances and thereby used to determine a user's gazing direction or focal distance. By selecting each capacitance sensor 645 to have a different capacitance value, controller 630 has improved differentiation to determine which capacitance sensor 645 has been overlapped by an eyelid. The capacitance values of the different sized capacitance sensors 645 will change by different amounts when overlaid. Capacitive sensor system 635 does not entirely encircle accommodation actuator 615. Rather, in the illustrated embodiment, capacitive sensor system 635 is located in a lower quadrant closest to a user's nose for a rotationally-stable contact lens. It is anticipated that this quadrant will provide increased sensitivity for distinguishing near-field activities since eyes move down and inward when reading. In one embodiment, the lower, inner quadrant is populated with a higher density of capacitance sensor than the other quadrants for increased sensitivity in this region.

Figure 6C:
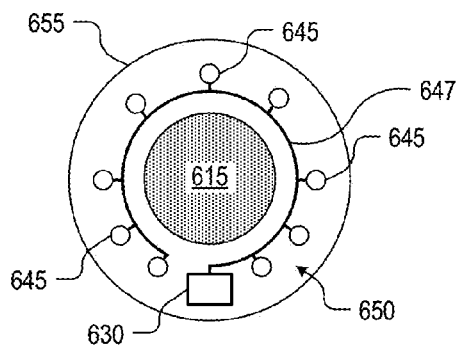

FIG. 6C illustrates a capacitive sensor system 650 disposed within an eye-mountable device 655. Capacitive sensor system 650 is similar to capacitive sensor system 635 illustrated in FIG. 6B, but includes a greater number of discrete capacitance sensors 645 more fully encircling accommodation actuator 615. Capacitive sensor system 650 is well suited for non-rotationally stable contact lens embodiments since it cannot be anticipated which quadrant of eye-mountable device 655 will end up being the lower inward quadrant closest to the user's nose.

Figure 6D:
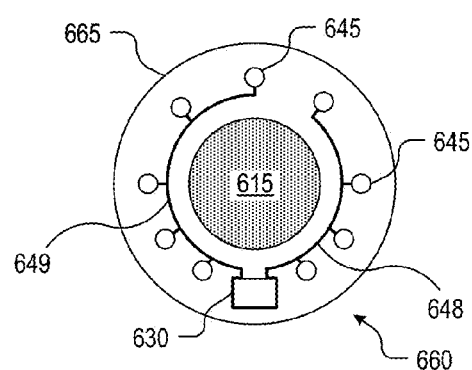

FIG. 6D illustrates a capacitive sensor system 660 disposed within an eye-mountable device 665. Capacitive sensor system 660 includes multiple branches 648 and 649 of parallel coupled discrete capacitance sensors 645. Each branch 648 or 649 has an independent read-line connection to controller 630. In one embodiment, the multiple branches share a common ground (not illustrated). The capacitance sensors 645 may each have the same or different capacitance values. Increasing the number of independent read-line branches provides greater differentiation to disambiguate between scenarios that cause similar changes in capacitance values thereby improving gaze direction sensing. However, this should be balanced with the cost and complexity associated with increased inputs on controller 630 and trace lines. Although FIG. 6D illustrates just two independent branches 648 and 649, it should be appreciated that more than two independent branches may be implemented.

Figure 6E:
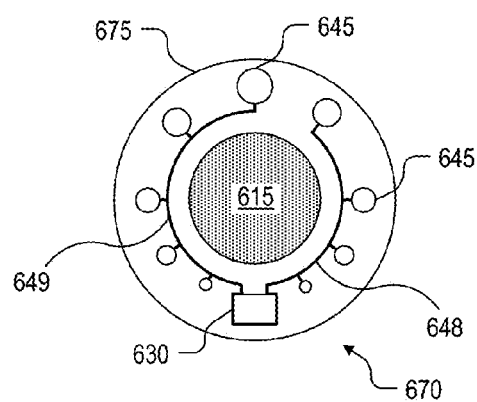

FIG. 6E illustrates a capacitive sensor system 670 disposed within an eye-mountable device 665. Capacitive sensor system 670 includes multiple branches 648 and 649 of parallel coupled discrete capacitance sensors 645. Capacitive sensor system 670 is similar to capacitive sensor system 660, except that the capacitance values of each discrete capacitance sensor 645 vary in sensitivity (capacitance) in opposite directions around the perimeter of eye-mountable device 675. This configuration is anticipated to discriminate absolute rotational position as well as eyelid coverage.

It should be appreciated that the embodiments illustrated in FIGS. 6A-6E may be combined into hybrid embodiments. For example, in one hybrid embodiment (combination of FIG. 6A and 6E), two independent elongated capacitors may be used, which vary in amount of separation between their respective electrodes, but vary in opposite directions along their lengths. This may be used to provide both eyelid position information and information about the amount of eyelid coverage. For example, a first capacitor 1 separation distance between its electrodes may vary with $E1(x)=A*x$, and second capacitor 2 separation distance between its electrodes may vary with $E2(x)=A*(L-x)$, where L is the length of the electrode, A is the rate of scaling, and $E1(x)$ and $E2(x)$ are the amount of electrode separation. In this example, the distance is linearly scaled. However, distance may instead be scaled in a non-linear ways to provide linearly or non-linearly changing capacitance changes relative to eyelid coverage/position.

Figure 7A:
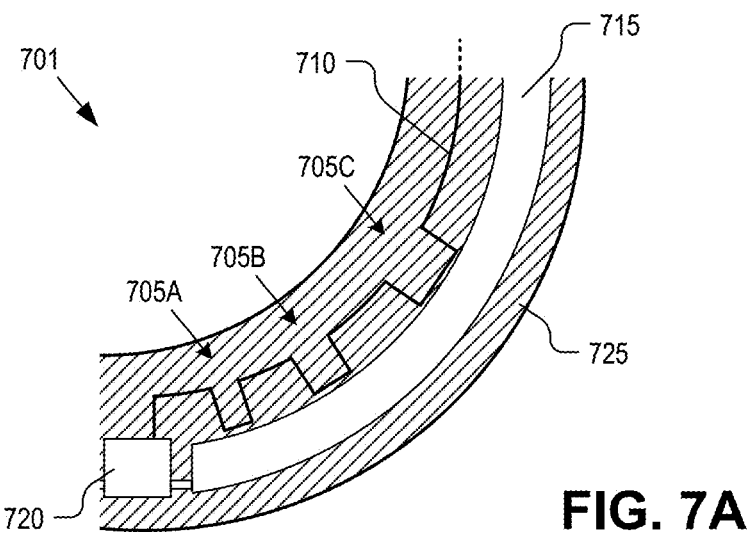
FIG. 7A illustrates discrete capacitor sensors coupled in parallel between a common read-line and a common ground that are implemented with variable parallel length sections, in accordance with an embodiment of the disclosure.

FIG. 7A illustrates a portion of a capacitive sensor system 701, in accordance with an embodiment of the disclosure. Capacitive sensor system 701 includes discrete capacitance sensors 705A-C coupled in parallel between a common read-line 710 and a common ground 715. Controller 720, read-line 710, and common ground 715 are all disposed on substrate 725, which is embedded within an enclosure material of an eye-mountable device. Common read-line 710 is coupled to a single input into controller 720. As such, the capacitance value of each capacitance sensor 705A-C adds together for a single collective capacitance value read via common read-line 710.

Capacitance sensors 705A-C are implemented with variable length sections of read-line 710 that run adjacent and substantially parallel to portions of common ground 715. The variable length sections give each capacitance sensor 705A-C a different capacitance value and therefore a different capacitance change when overlapped by an eyelid. The distinct change values enable controller 720 to determine which capacitance sensor 705A-C has been overlaid at a given moment.

Figure 7B:
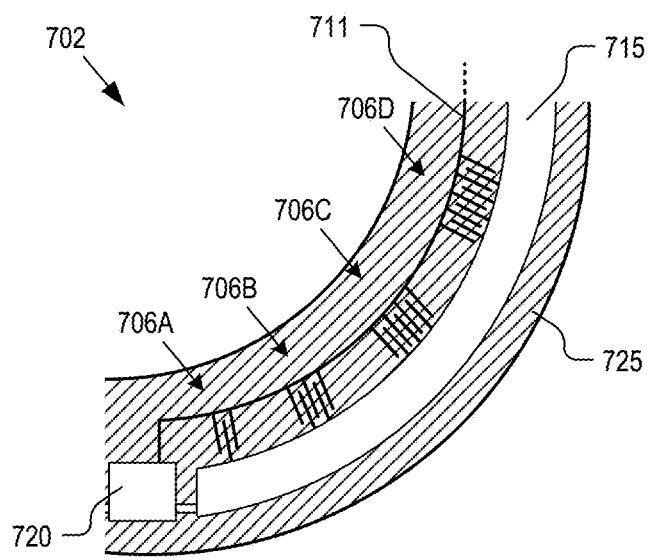
FIG. 7B illustrates discrete capacitor sensors coupled in parallel between a common read-line and a common ground that are implemented with interdigitated fingers, in accordance with an embodiment of the disclosure.

FIG. 7B illustrates a portion of a capacitive sensor system 702, in accordance with an embodiment of the disclosure. Capacitive sensor system 702 includes discrete capacitance sensors 706A-D coupled in parallel between a common read-line 711 and a common ground 715. Controller 720, read-line 711, and common ground 715 are all disposed on substrate 725, which is embedded within an enclosure material of an eye-mountable device. Common read-line 711 is coupled to a single input into controller 720. As such, the capacitance value of each capacitance sensor 706A-D adds together for a single collective capacitance value read via common read-line 711. Capacitance sensors 706A-D are implemented with read-line fingers that are interdigitated with common ground fingers. Each capacitance sensor 706A-D has a different number of interdigitated fingers resulting in each capacitance sensor 706A-D having a different capacitance value and therefore a different capacitance change when overlapped by an eyelid. The distinct change values enable controller 720 to determine which capacitance sensor 706A-D has been overlaid at a given moment.

In the illustrated embodiments, common ground 715 is implemented by grounding antenna 140 and time sharing it by controller 720 between wireless communications and capacitive gaze sensing. In other embodiments, common ground 715 may be an independent electrode separate from antenna 140. Although FIGS. 7A and 7B only illustrate three or four capacitance sensors 705 or 706, more or less parallel coupled capacitance sensors may share a common read-line.

Figure 8A:
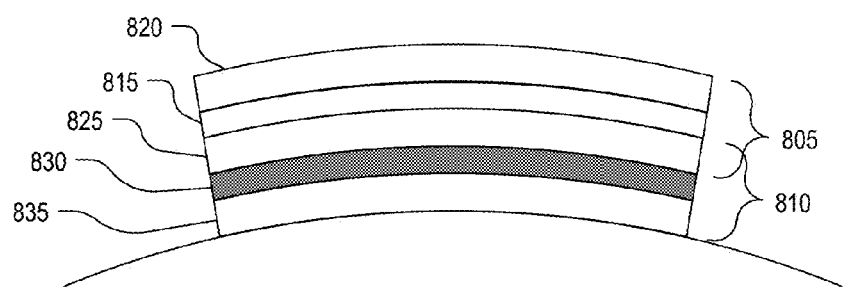
FIG. 8A illustrates a vertically stacked implementation of a capacitive sensor system and an accommodation actuator, in accordance with an embodiment of the disclosure.

FIG. 8A illustrates how a capacitive sensor system 805 can be vertically stacked over an accommodation actuator 810, in accordance with an embodiment of the disclosure. For example, capacitive sensor system 805 may be implemented with a transparent dielectric layer 815 sandwiched between transparent conductive layers 820 and 825. Of course, the transparent conductive layers 820 and 825 can be patterned into traces and electrodes to form the read-lines and capacitor electrode terminals. In one embodiment, accommodation actuator 810 is implemented by sandwiching a liquid crystal layer 830 between transparent conductive layers 825 and 835. In one embodiment, the transparent conductive layers 820, 825, and 835 are implemented using indium tin oxide ("ITO") or other transparent conductors.

Figure 8B:
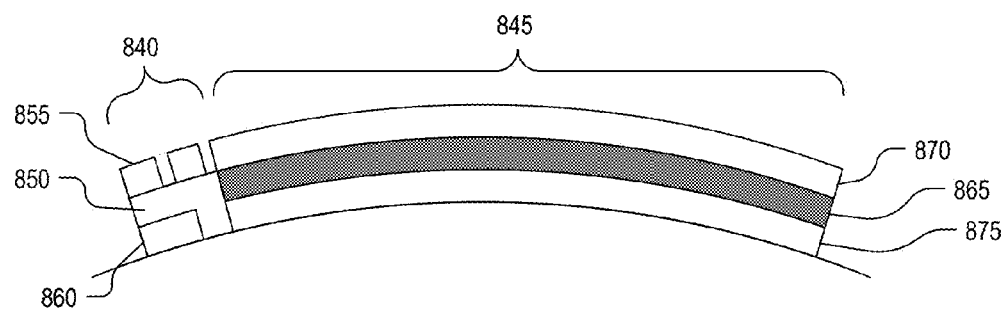
FIG. 8B illustrates an in-plane lateral implementation of a capacitive sensor system and an accommodation actuator, in accordance with an embodiment of the disclosure.

FIG. 8B illustrates how a capacitive sensor system 840 can be integrated laterally in-plane with an accommodation actuator 845, in accordance with an embodiment of the disclosure. For example, capacitive sensor system 840 may be implemented with a dielectric layer 850 sandwiched between conductive layers 855 and 860. The illustrated embodiment of accommodation actuator 845 includes a liquid crystal layer 865 sandwiched between transparent conductive layers 870 and 875. The lateral in-plane configuration of FIG. 8B enables the use of nontransparent conductors (e.g., aluminum, gold, etc.) for the conductive layers 855 and 860 forming the capacitor electrode terminals, since the capacitors are positioned along the perimeter of the eye-mountable device.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An eye-mountable device, comprising:
    an enclosure material having a first surface and a second surface, wherein the first surface is configured to be removeably mounted over a cornea and the second surface is configured to be compatible with eyelid motion when the first surface is so mounted;
    a capacitive sensor system disposed within the enclosure material, wherein the capacitive sensor system has at least one capacitance value that varies with changes in a gazing direction of the cornea; and
    a controller disposed within the enclosure material and electrically connected to the capacitive sensor system, wherein the controller is configured to measure the capacitance value of the capacitive sensor system to detect the changes in the gazing direction.

2. The eye-mountable device of claim 1, further comprising:
    an accommodation actuator disposed within the enclosure material and electrically connected to the controller, wherein the controller is configured to electrically manipulate the accommodation actuator to automatically change an optical power of the eye-mountable device in response to changes in the capacitance value.

3. The eye-mountable device of claim 2, wherein the accommodation actuator comprises a see-through electro-active optical material having a refractive index that changes under electrical influence of the controller.

4. The eye-mountable device of claim 2, wherein the accommodation actuator comprises a see-through liquid crystal layer having a refractive index that changes under electrical influence of the controller.

5. The eye-mountable device of claim 2, wherein the capacitive sensor system comprises:
    a single elongated capacitor that partially encircles the accommodation actuator.

6. The eye-mountable device of claim 2, further comprising:
    a substrate having a ring shape disposed within the enclosure material, wherein the controller and capacitive sensor system are disposed on the substrate, wherein the ring shape of the substrate encircles the accommodation actuator.

7. The eye-mountable device of claim 2, wherein the capacitive sensor system and the accommodation actuator are disposed with a multi-layer material stack and wherein the capacitive sensor system is disposed within the multi-layer material stack closer to an eyelid than the accommodation actuator when the first surface is so mounted.

8. The eye-mountable device of claim 2, wherein the capacitive sensor system and the accommodation actuator are disposed lateral to each other.

9. The eye-mountable device of claim 1, wherein the capacitive sensor system comprises:
    a plurality of discrete capacitance sensors disposed in a peripheral region of the enclosure material.

10. The eye-mountable device of claim 9, wherein the plurality of discrete capacitance sensors are coupled in parallel with each other and share a common read-line connection to the controller and share a common ground.

11. The eye-mountable device of claim 10, wherein each of the discrete capacitance sensors coupled in parallel has a different capacitance that changes by a different amount when overlaid by an eyelid.

12. The eye-mountable device of claim 10, wherein the plurality of discrete capacitance sensors comprises varying parallel length sections of the common read-line that run adjacent to the common ground.

13. The eye-mountable device of claim 10, wherein the plurality of discrete capacitance sensors comprises varying a number of read-line fingers that are interdigitated with common ground fingers for the different ones of the discrete capacitance sensors.

14. The eye-mountable device of claim 9, wherein the plurality of discrete capacitance sensors are arranged into multiple branches with each of the multiple branches having an independent read-line connection to the controller, wherein the discrete capacitance sensors within a given one of the multiple branches are coupled in parallel with each other.

15. The eye-mountable device of claim 9, wherein the eye-mountable device is a rotationally-stable contact lens and wherein a density of the discrete capacitors is higher in a lower quadrant closest to a user's nose than in one or more other quadrants of the eye-mountable device.

16. A contact lens, comprising:
    an enclosure material having a first surface and a second surface, wherein the first surface is configured to be removeably mounted over a cornea and the second surface is configured to be compatible with eyelid motion when the first surface is so mounted;
    a capacitive sensor system disposed within the enclosure material, wherein the capacitive sensor system has at least one capacitance value that varies with changes in a gazing direction of the cornea;
    an accommodation actuator disposed within the enclosure material and located to overlay at least a central portion of the cornea when the first surface is so mounted; and a controller disposed within the enclosure material and electrically connected to the capacitive sensor system and the accommodation actuator, wherein the controller includes logic that when executed by the controller causes the controller perform operations including:

monitoring the capacitance value of the capacitive sensor system to detect in real-time the changes in the gazing direction; and electrically manipulating the accommodation actuator to automatically change an optical power of the contact lens in response to changes in the capacitance value.

17. The contact lens of claim 16, wherein the accommodation actuator comprises a see-through electro-active optical material having a refractive index that changes under electrical influence of the controller.

18. The contact lens of claim 16, wherein the accommodation actuator comprises a see-through liquid crystal layer having a refractive index that changes under electrical influence of the controller.

19. The contact lens of claim 16, wherein the capacitive sensor system comprises:

a single elongated capacitor that partially encircles the accommodation actuator.

20. The contact lens of claim 19, wherein the capacitive sensor system further comprises:

a second elongated capacitor that also partially encircles the accommodation actuator, wherein the first and second elongated capacitors have linearly capacitances that change along their lengths in opposite directions from each other.

21. The contact lens of claim 16, wherein the capacitive sensor system comprises:

a plurality of discrete capacitance sensors disposed peripherally to the accommodation actuator.

22. The contact lens of claim 21, wherein the plurality of discrete capacitance sensors are coupled in parallel with each other.

23. The contact lens of claim 22, wherein each of the discrete capacitance sensors coupled in parallel has a different capacitance that changes by a different amount when overlaid by an eyelid.

24. The contact lens of claim 21, wherein the plurality of discrete capacitance sensors are arranged into multiple branches with each of the multiple branches having an independent read line connection to the controller, wherein the discrete capacitance sensors within a given one of the multiple branches are coupled in parallel with each other.

25. The contact lens of claim 21, wherein the eye-mountable device is a rotationally-stable contact lens and wherein a density of the discrete capacitors is higher in a lower quadrant closest to a user's nose than in one or more other quadrants of the eye-mountable device.

26. The contact lens of claim 16, further comprising:

a substrate having a ring shape disposed within the enclosure material, wherein the controller and capacitive sensor system are disposed on the substrate, wherein the ring shape of the substrate encircles the accommodation actuator.

27. The contact lens of claim 26, further comprising:

a battery disposed on the substrate within the enclosure material; and an antenna disposed on the substrate and electrically connected to the controller, the antenna configured to provide wireless communication with the controller and inductive charging of the battery.

28. The contact lens of claim 27, wherein the controller further includes logic that when executed by the controller causes the controller to perform operations including:

alternately sharing the antenna between wireless communications and as a common ground for a plurality of parallel coupled discrete capacitors during capacitive gaze sensing.

* * * * *